US00RE38912E

(19) United States
(12) Reissued Patent
Walz et al.

(10) Patent Number: US RE38,912 E
(45) Date of Reissued Patent: Dec. 6, 2005

(54) PROCESS FOR PREPARING POWDER FORMULATIONS

(75) Inventors: Michael Walz, Bingen (DE); Georg Boeck, Mainz (DE)

(73) Assignee: Boehringer Ingelheim Pharma KG, Ingelheim (DE)

(21) Appl. No.: 10/766,748

(22) Filed: Jan. 28, 2004

Related U.S. Patent Documents

Reissue of:
(64) Patent No.: 6,585,959
Issued: Jul. 1, 2003
Appl. No.: 09/977,911
Filed: Oct. 11, 2001

U.S. Applications:
(60) Provisional application No. 60/252,683, filed on Nov. 22, 2000.

(30) Foreign Application Priority Data

Oct. 12, 2000 (DE) ..... 100 50 635
Aug. 10, 2001 (DE) ..... 101 38 022

(51) Int. Cl.[7] ..... A61K 9/14; A61K 9/16; A61L 9/04; A61F 13/02
(52) U.S. Cl. ..... 424/46; 424/434; 424/435; 424/489; 424/493
(58) Field of Search ..... 424/46, 434, 435, 424/489, 493

(56) References Cited

U.S. PATENT DOCUMENTS 3,634,582 A * 1/1972 Hartley et al.
3,860,618 A * 1/1975 Hartley et al.
3,957,965 A * 5/1976 Hartley et al.
5,478,578 A * 12/1995 Arnold et al.
6,183,782 B1 * 2/2001 Hallworth
6,221,338 B1 * 4/2001 Staniforth
6,284,287 B1 9/2001 Sarlikiotis et al.

FOREIGN PATENT DOCUMENTS

DE 44 25 255 1/1996
FR 8.142 M A * 8/1970
WO WO93/11746 A1 * 6/1993
WO WO 93/11746 A1 * 6/1993
WO WO 95/11666 A1 * 5/1995
WO WO 95/24889 A1 * 9/1995
WO WO 00/28979 A1 * 5/2000
WO WO 00/47200 A1 * 8/2000

OTHER PUBLICATIONS

Derwent Abstract: AN 1966–36583F[00] WPIDS (French Patent 8.142M; Fisons Pharm. Ltd).*

Bechtold–Peters, K. et al; "Inhalable Powder Containing Tiotropium"; U.S. Appl. No. 09/975,418; Nov. 11, 2001.*

* cited by examiner

*Primary Examiner*—Carlos A. Azpuru
(74) *Attorney, Agent, or Firm*—Michael Morris; Andrea D. Small; MaryEllen M. Devlin

(57) ABSTRACT

The invention relates to a new process for producing powdered preparations for inhalation.

34 Claims, No Drawings

PROCESS FOR PREPARING POWDER FORMULATIONS

Matter enclosed in heavy brackets [ ] appears in the original patent but forms no part of this reissue specification; matter printed in italics indicates the additions made by reissue.

RELATED APPLICATIONS

Benefit of U.S. Provisional Application Serial No. 60/252,683, filed on Nov. 22, 2000 is hereby claimed, and said Provisional Application is herein incorporated by reference.

The invention relates to a new process for preparing powdered preparations for inhalation.

BACKGROUND OF THE INVENTION treating a number of complaints, particularly respiratory diseases, it is useful to administer the active substance by inhalation. In addition to the administration of therapeutically active compounds in the form of metered aerosols and inhalable solutions, the use of inhalable powders containing active substance is of particular importance.

With active substances which have a particularly high efficacy, only small amounts of the active substance are needed per single dose to achieve the desired therapeutic effect. In such cases, the active substance has to be diluted with suitable excipients in order to prepare the inhalable powder. Because of the large amount of excipient, the properties of the inhalable powder are critically influenced by the choice of excipient.

In powder mixture technology, it is conventional to use mixing processes based on the dilution method. All the active substance is used and then excipient is added in proportions of 1:1, 1:2 or 1:4 and they are mixed together. More excipient is then added to the resulting mixtures in comparable proportions. This procedure is usually repeated until all the excipient has been added. The drawback of this type of procedure it that is some cases there are problems of homogeneity. These arise particularly with mixtures in which the substances have a widely varying spectrum of particle sizes. This is particularly apparent in powder mixtures in which the substance having the smaller particle size distribution, the active substance, makes up only a very small proportion of the total amount of powder.

The problem of the present invention is therefore to provide a process which can be used to produce inhalable powders characterised by a high degree of homogeneity in the sense of a uniformity of content.

DETAILED DESCRIPTION OF THE INVENTION

It was found that, surprisingly, the problem outlined above can be solved by means of a process in which the substance with the smaller particle size distribution can be added to the substance with the coarser particle size distribution by a layered mixing process.

The process according to the invention for preparing inhalable powders is characterised in that N+m substantially equal portions of the substance having a larger particle size distribution and N equal portions of the substance having a smaller particle size distribution are placed in alternate layers in a suitable mixing vessel and after they have all been added the 2N+m layers of the two components are mixed together using a suitable mixer, a portion of the substance having the larger particle size being put in first, while N is an integer >0, preferably >5, and m denotes 0 or 1.

Preferably, the individual fractions are added in layers through a suitable screening apparatus. If desired, once the mixing process is finished, the entire powder mixture can be subjected to one or more additional screening processes. In the process according to the invention, N is naturally dependent inter alia on the total quantity of powder mixture to be produced. When producing smaller batches, the desired effect of high homogeneity in the sense of uniformity of content can be achieved with a smaller N. In principle, it is preferable according to the invention if N is at least 10 or more, more preferably 20 or more, better still 30 or more. The greater N is and, as a result, the greater the total number of layers of the powder fractions formed, the more homogeneous the powder mixture becomes in the sense of uniformity of content.

The number m may represent 0 or 1 within the scope of the process according to the invention. If m denotes 0 the last fraction added to the mixing apparatus, preferably screened into it, in a layer is the last portion of the substance with a smaller particle size distribution. If m represents the number 1, the last fraction added to the mixing apparatus, preferably screened into it, in a layer is the last portion of the substance with a larger particle size distribution. This may prove advantageous inasmuch as, when m=1, any residues of the last fraction of the substance with the finer particle size distribution still remaining in the screening unit can be carried into the mixing unit by means of the last portion of excipient.

Within the scope of the present invention, unless otherwise defined, the substance with the smaller particle size distribution, which is very finely ground and is present in the resulting powder formulation in a very small proportion by mass, represents the active substance. Within the scope of the present invention, unless otherwise defined, the substance with the larger particle size distribution, which is coarsely ground and is present in the resulting powder formulation in a large proportion by mass, represents the excipient.

The present invention relates in particular to a process for preparing inhalable powders containing less than 5%, preferably less than 2%, most preferably less than 1% of active substance mixed with a physiologically acceptable excipient. A preferred process according to the invention is a process for preparing inhalable powders containing 0.04 to 0.8%, most preferably 0.08 to 0.64%, better still 0.16 to 0.4% of active substance mixed with a physiologically acceptable excipient.

The active substance used according to the invention preferably has an average particle size of 0.5 to 10 $\mu$m, preferably 1 to 6 $\mu$m, most preferably 2 to 5 $\mu$m. The excipient which may be used in the process according to the invention preferably has an average particle size of 10 to 100 $\mu$m, preferably 15 to 80 $\mu$m, most preferably 17 to 50 $\mu$m. Particularly preferred according to the invention are processes for preparing inhalable powders wherein the excipient has an average particle size of 20–30 $\mu$m.

The two components are preferably added through a screening granulator with a mesh size of 0.1 to 2 mm, most preferably 0.3 to 1 mm, even more preferably 0.3 to 0.6 mm.

Preferably, the first portion of the N+m portions of the excipient is put in first, and then the first portion of the N portions of the active substance is placed in the mixing container. Whereas within the scope of the process according to the invention the individual components are normally added in roughly equal portions, it may be advantageous in some cases if the first of the N+m portions of excipient which is put into the mixing apparatus has a larger volume than the subsequent portions of excipient. Preferably, the two components are added alternately through a screening unit and in more than 20, preferably more than 25, most preferably more than 30 layers. For example, with a desired total amount of powder of 30–35 kg containing 0.3–0.5% of active substance, for example, and using common excipients, the two components can be screened in in about 30 to 60 layers each (N=30–60). The upper limit of 60 layers mentioned above is given purely from the point of view of economy of the process. It should not be regarded in any way as restricting the number of possible layers according to the invention. As will be clearly apparent to anyone skilled in the art, the process can equally well be carried out with N>60 to achieve the desired effect of the maximum possible homogeneity of the powder mixture.

In some cases the excipient may also consist of a mixture of coarser excipient with an average particle size of 15 to 80 μm and finer excipient with an average particle size of 1 to 9 μm, wherein the proportion of finer excipient in the total quantity of excipient may be 1 to 20%. If the inhalable powders which may be produced using the process according to the invention contain a mixture of coarser and finer excipient fractions, it is preferable according to the invention to prepare inhalable powders wherein the coarser excipient has an average particle size of 17 to 50 μm, most preferably 20 to 30 μm, and the finer excipient has an average particle size of 2 to 8 μm, most preferably 3 to 7 μm. By average particle size is meant here the 50% value of the volume distribution measured with a laser diffractometer using the dry dispersion method. In the case of an excipient mixture of coarser and finer excipient fractions, the preferred processes according to the invention are those that produce inhalable powders in which the proportion of finer excipient constitutes 3 to 15%, most preferably 5 to 10% of the total amount of excipient.

The percentages given within the scope of the present invention are always percent by weight.

If the excipient used is one of the abovementioned mixtures of coarser excipient and finer excipient, it is again expedient according to the invention to produce the excipient mixture using the process according to the invention from N roughly equal portions of the finer excipient fraction with N+m roughly equal portions of the coarser excipient fraction. In such a case it is advisable first to generate the abovementioned excipient mixture from the abovementioned excipient fractions, and then to produce from it the total mixture including the active substance using the process according to the invention.

For example, the excipient mixture may be obtained as follows, using the process according to the invention. The two components are preferably added through a screening granulator with a mesh size of 0.1 to 2 mm, most preferably 0.3 to 1 mm, even more preferably 0.3 to 0.6 mm. Preferably the first fraction of the N+m portions of the coarser excipient is put in first and then the first portion of the N portions of the finer excipient fraction is added to the mixing container. The two components are added alternately by screening them in in layers.

After the preparation of the excipient mixture, the inhalable powder is produced from the mixture and the desired active substance using the process according to the invention. The two components are preferably added through a screening granulator with a mesh size of 0.1 to 2 mm, most preferably 0.3 to 1 mm, even more preferably 0.3 to 0.6 mm.

Preferably, the first portion of the N+m portions of the excipient mixture is put in and then the first portion of the N portions of the active substance is added to the mixing container. The two components are preferably added through a screening unit in alternate layers, in more than 20, preferably more than 25, most preferably more than 30 layers. For example, with a desired total amount of powder of 30–35 kg containing 0.3–0.5% of active substance, for example, and using common excipients, the two components can be screened in in about 30 to 60 layers each (N=30–60). As will be clearly apparent to anyone skilled in the art, the process can equally well be carried out with N>60 to achieve the desired effect of the maximum possible homogeneity of the powder mixture. The inhalable powders which may be obtained using the method of preparation according to the invention may contain, in general, any active substances which may reasonably be administered by inhalation for therapeutic purposes. Preferably, the active substances used are selected, for example, from among the betamimetics, anticholinergics, corticosteroids and dopamine agonists.

Example of betamimetics which may be used are preferably compounds selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tulobuterol, mabuterol, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-on, 1-(4-amino-3-chloro-5-trifluoromethylphenyl)-2-tert.butylamino)ethanol and 1-(4-ethoxycarbonylamino-3-cyano-5-fluorophenyl)-2-(tert.butylamino)ethanol, optionally in the form of their racemates, their enantiomers, their diastereomers, as well as optionally their pharmacologically acceptable acid addition salts and hydrates. It is particularly preferable to use, as betamimetics, active substances of this kind selected from among fenoterol, formoterol, salmeterol, mabuterol, 1-[3-(4-methoxybenzylamino)-4-hydroxyphenyl]-2-[4-(1-benzimidazolyl)-2-methyl-2-butylamino]-ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4II-1,4-benzoxazin-8-yl]-2-{4-[3-(4-methoxyphenyl)-1,2,4-triazol-3-yl]-2-methyl-2-butylamino}ethanol, optionally in the form of their racemates, their enantiomers, their diastereomers, as well as optionally their pharmacologically acceptable acid addition salts and hydrates. Of the betamimetics mentioned above, the compounds formoterol and salmeterol, optionally in the form of their racemates, their enantiomers, their diastereomers, as well as optionally their pharmacologically acceptable acid addition salts and hydrates, are particularly important.

The acid addition salts of the betamimetics selected from among the hydrochloride, hydrobromide, sulphate, phosphate, fumarate, methanesulphonate and xinafoate are preferred according to the invention. In the case of salmeterol, the salts selected from among the hydrochloride, sulphate and xinafoate are particularly preferred, especially the sulphates and xinafoates. Of outstanding importance according to the invention are salmeterol×½$II_2SO_4$ and salmeterol xinafoate. In the case of formoterol, the salts selected from among the hydrochloride, sulphate and fumarate are particularly preferred, especially the hydrochloride and fumarate. Of outstanding importance according to the invention is formoterol fumarate.

Anticholinergics which may be used in the processes according to the invention are preferably salts selected from among tiotropium salts, oxitropium salts and ipratropium salts, of which tiotropium and ipratropium salts are particularly preferred. In the abovementioned salts the cations tiotropium, oxitropium and ipratropium are the pharmacologically active ingredients. By the salts which may be used within the scope of the present invention are meant the compounds which contain, in addition to tiotropium, oxitropium or ipratropium as counter-ion (anion) chloride, bromide, iodide, sulphate, methanesulphonate or paratoluenesulphonate. Within the scope of the present invention, of all the salts of the abovementioned anticholinergics, the methanesulphonate, chloride, bromide and iodide are preferred, the methanesulphonate or bromide being especially preferred. Of outstanding importance according to the invention are the anticholinergics selected from among tiotropium bromide, oxitropium bromide and ipratropium bromide. Tiotropium bromide is particularly preferred. The abovementioned anticholinergics may optionally occur in the form of their solvates or hydrates. In the case of tiotropium bromide, for example, tiotropium bromide monohydrate is particularly important according to the invention.

Within the scope of the present invention, the term corticosteroids denotes compounds selected from among flunisolide, beclomethasone, triamcinolone, budesonide, fluticasone, mometasone, ciclesonide, rofleponide, GW 215864, KSR 592, ST-126 and dexamethasone. The preferred corticosteroids within the scope of the present invention are those selected from among flunisolide, beclomethasone, triamcinolone, budesonide, fluticasone, mometasone, ciclesonide and dexamethasone, while budesonide, fluticasone, mometasone and ciclesonide, especially budesonide and fluticasone, are of particular importance. The term steroids may be used on its own, within the scope of the present patent application, instead of the term corticosteroids. Any reference to steroids within the scope of the present invention also includes a reference to salts or derivatives which may be formed from the steroids. Examples of possible salts or derivatives include: sodium salts, sulphobenzoates, phosphates, isonicotinates, acetates, propionates, dihydrogen phosphates, palmitates, pivalates or furoates. The corticosteroids may optionally also be in the form of their hydrates.

Within the scope of the present invention, the term dopamine agonists denotes compounds selected from among bromocriptine, cabergolin, alpha-dihydroergocryptine, lisuride, pergolide, pramipexol, roxindol, ropinirol, talipexol, tergurid and viozan. It is preferable within the scope of the present invention to use dopamine agonists selected from among pramipexol, talipexol and viozan, pramipexol being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

The process according to the invention for preparing powder mixtures for inhalation may be used to prepare powders which contain one or more of the abovementioned active ingredients. If, for example, inhalable powders are to be prepared in which the pharmaceutically active ingredients consist of two different active substances, this can be achieved using the process according to the invention, for example, by screening N+m roughly equal portions of excipient or excipient mixture with O roughly equal portions of one active substance component and P roughly equal portions of the other active substance component into the mixing apparatus in alternate layers. The number of fractions P and O may be selected, for example, so that P+O=N. If the process according to the invention is to be used to prepare inhalable powders which contain two active ingredients, for example, preferred possible combinations of active substances might consist of a combination of one of the abovementioned anticholinergics with one of the abovementioned corticosteroids or a combination of one of the abovementioned anticholinergics with one of the abovementioned betamimetics.

Examples of physiologically acceptable excipients which may be used to prepare the inhalable powders according to the invention include, for example, monosaccharides (e.g. glucose or arabinose), disaccharides (e.g. lactose, saccharose, maltose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

The inhalable powders which may be obtained by the preparation process according to the invention are characterised by an exceptional degree of homogeneity in terms of uniformity of content. This is in a range of <8%, preferably <6%, most preferably <4%. The inhalable powders which may be prepared according to the invention may possibly even have levels of homogeneity, in the sense of single dose accuracy, of <3%, possibly <2%. Thus, in a further aspect, the present invention relates to inhalable powders as such which may be obtained by the preparation process according to the invention.

The inhalable powders which may be obtained by the process according to the invention may for example be administered using inhalers which meter a single dose from a reservoir by means of a measuring chamber (e.g. according to U.S. Pat. No. 4,570,630A) or by other means (e.g. according to DE 36 25 685 A). Preferably, however, the inhalable powders which may be obtained according to the invention are packed into capsules (to make so-called inhalettes), which are used in inhalers such as those described in WO 94/28958, for example. If the inhalable powder obtained by the process according to the invention is to be packed into capsules (inhalettes) in accordance with the preferred application mentioned above, it is advisable to fill the capsules with amounts of from 3 to 10 mg, preferably from 4 to 6 mg of inhalable powder per capsule, this amount depending to a large extent on the choice of active substance used. In the case of the active substance tiotropium bromide, the capsules contain between 1.2 and 80 μg of tiotropium cation, for the amounts of filling mentioned above. With a filling of 4 to 6 mg of inhalable powder per capsule, the preferred amount for tiotropium bromide, the content of tiotropium per capsule is between 1.6 and 48 μg, preferably between 3.2 and 38.4 μg, most preferably between 6.4 and 24 μg. A content of 18 μg of tiotropium, for example, corresponds to a content of about 21.7 μg of tiotropium bromide.

Consequently, capsules containing 3 to 10 mg of powder for inhalation preferably hold between 1.4 and 96.3 μg of tiotropium bromide, according to the invention. When the filling is from 4 to 6 mg of inhalable powder per capsule, as is preferred, each capsule contains between 1.9 and 57.8 μg, preferably between 3.9 and 46.2 μg, most preferably between 7.7 and 28.9 μg of tiotropium bromide. A content of 21.7 μg of tiotropium bromide, for example, corresponds to a content of about 22.5 μg of tiotropium bromide monohydrate.

Consequently, capsules containing 3 to 10 mg of powder for inhalation preferably hold between 1.5 and 100 μg of tiotropium bromide monohydrate. When the filling is from 4 to 6 mg of inhalable powder per capsule, as is preferred, each capsule contains between 2 and 60 μg, preferably between 4 and 48 μg, most preferably between 8 and 30 μg of tiotropium bromide monohydrate.

The Examples which follow describe a possible method of carrying out the process according to the invention, taking a powder mixture containing tiotropium bromide monohydrate as the example. The fact that this process described by way of example can be used directly for preparing inhalable powders which contain one or more of the other active substances mentioned above will be apparent to anyone skilled in the art. Accordingly, the following Examples serve only to illustrate the present invention further without restricting its scope to the embodiments provided hereinafter by way of example.

Starting Materials

In the Examples which follow, lactose-monohydrate (200M) is used as the coarser excipient. It may be obtained, for example, from Messrs DMV International, 5460 Veghel/NL under the product name Phannatose 200M.

In the Examples which follow, lactose-monohydrate (5μ) is used as the finer excipient. It may be obtained from lactose-monohydrate 200M by conventional methods (micronising). Lactose-monohydrate 200M may be obtained, for example, from Messrs DMV International, 5460 Veghel/NL under the product name Pharmatose 200M.

Preparation of Tiotropium Bromide Monohydrate:

15.0 kg of tiotropium bromide, which may be prepared as disclosed in EP 418 716 A1, are added to 25.7 kg of water in a suitable reaction vessel. The mixture is heated to 80–90° C. and stirred at constant temperature until a clear solution is formed. Activated charcoal (0.8 kg), moistened with water, is suspended in 4.4 kg of water, this mixture is added to the solution containing the tiotropium bromide and rinsed with 4.3 kg of water. The mixture thus obtained is stirred for at least 15 min at 80–90° C. and then filtered through a heated filter into an apparatus which has been preheated to an outer temperature of 70° C. The filter is rinsed with 8.6 kg of water. The contents of the apparatus are cooled at 3–5° C. every 20 minutes to a temperature of 20–25° C. The apparatus is further cooled to 10–15° C. using cold water and crystallisation is completed by stirring for at least one hour. The crystals are isolated using a suction drier, the crystal slurry isolated is washed with 9 liters of cold water (10–15° C.) and cold acetone (10–15° C.). The crystals obtained are dried in a nitrogen current at 25° C. over 2 hours. Yield: 13.4 kg of tiotropium bromide monohydrate (86% of theory)

The crystalline tiotropium bromide monohydrate thus obtained is micronised by known methods, to bring the active substance into the average particle size which meets the specifications according to the invention.

For the purposes of the present invention, the average particle size is the value in μm at which 50% of the particles from the volume distribution have a particle size which is smaller than or equal to the value specified. The laser diffraction/dry dispersal method of measurement is used to determine the total distribution of the particle size distribution.

The method of determining the average particle size of the various ingredients of the formulation according to the invention is described as follows.

A) Determining the Particle Size of Finely Divided Lactose:

Measuring Equipment and Settings:

The equipment is operated according to the manufacturer's instructions.

| | |
|---|---|
| Measuring equipment: | HELOS Laser-diffraction spectrometer (SympaTec) |
| Dispersing unit: | RODOS dry disperser with suction funnel, (SympaTec) |
| Sample quantity: | from 100 mg |
| Product feed: | Vibri Vibrating channel, Messrs. Sympatec |
| Frequency of vibrating channel: | 40 rising to 100% |
| Duration of sample feed: | 1 to 15 sec. (in the case of 100 mg) |
| Focal length: | 100 mm (measuring range: 0.9–175 μm) |
| Measuring time: | about 15 s (in the case of 100 mg) |
| Cycle time: | 20 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed:

At least 100 mg of the test substance are weighed onto a piece of card. Using another piece of card all the larger lumps are broken up. The powder is then sprinkled finely over the front half of the vibrating channel (starting about 1 cm from the front edge). After the start of the measurement the frequency of the vibrating channel is varied from about 40% up to 100% (towards the end of the measurement). The time taken to feed in the entire sample is 10 to 15 sec.

Determining the Particle Size of Micronised Tiotropium Bromide Monohydrate:

Measuring Equipment and Settings:

The equipment is operated according to the manufacturer's instructions.

| | |
|---|---|
| Measuring equipment: | Laser diffraction spectrometer (HELOS), Sympatec |
| Dispersing unit: | RODOS dry disperser with suction funnel, Sympatec |

-continued

| | |
|---|---|
| Sample quantity: | 50 mg–400 mg |
| Product feed: | Vibri Vibrating channel, Messrs. Sympatec |
| Frequency of vibrating channel: | 40 rising to 100% |
| Duration of sample feed: | 15 to 25 sec. (in the case of 200 mg) |
| Focal length: | 100 mm (measuring range: 0.9–175 μm) |
| Measuring time: | about 15 s (in the case of 200 mg) |
| Cycle time: | 20 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed:

About 200 mg of the test substance are weighed onto a piece of card. Using another piece of card all the larger lumps are broken up. The powder is then sprinkled finely over the front half of the vibrating channel (starting about 1 cm from the front edge). After the start of the measurement the frequency of the vibrating channel is varied from about 40% up to 100% (towards the end of the measurement). The sample should be fed in as continuously as possible. However, the amount of product should not be so great that adequate dispersion cannot be achieved. The time over which the entire sample is fed in is about 15 to 25 seconds for 200 mg, for example.

C) Determining the Particle Size of Lactose 200M:

Measuring Equipment and Settings:

The equipment is operated according to the manufacturer's instructions.

| | |
|---|---|
| Measuring equipment: | Laser diffraction spectrometer (HELOS), Sympatec |
| Dispersing unit: | RODOS dry disperser with suction funnel, Sympatec |
| Sample quantity: | 500 mg |
| Product feed: | Vibri Vibrating channel, Messrs. Sympatec |
| Frequency of vibrating channel: | 18 rising to 100% |
| Focal length (1): | 200 mm (measuring range: 1.8–350 μm) |
| Focal length (2): | 500 mm (measuring range: 4.5–875 μm) |
| Measuring time: | 10 s |
| Cycle time: | 10 ms |
| Start/stop at: | 1% on channel 19 |
| Pressure: | 3 bar |
| Vacuum: | maximum |
| Evaluation method: | HRLD |

Sample Preparation/Product Feed:

About 500 mg of the test substance are weighed onto a piece of card. Using another piece of card all the larger lumps are broken up. The powder is then transferred into the funnel of the vibrating channel. A gap of 1.2 to 1.4 mm is set between the vibrating channel and funnel. After the start of the measurement the amplitude setting of the vibrating channel is increased from 0 to 40% until a continuous flow of product is obtained. Then it is reduced to an amplitude of about 18%. Towards the end of the measurement the amplitude is increased to 100%.

Apparatus

The following machines and equipment, for example, may be used to prepare the inhalable powders according to the invention:

| | |
|---|---|
| Mixing container or powder mixer: | Gysowbeel mixer 200 L; type: DFW80N-4; made by: Messrs Engelsmann, D-67059 Ludwigsbafen. |
| Granulating sieve: | Quadro Cosnil; type: 197-S; made by: Messrs Joisten & Kettenbaum, D-51429 Bergisch-Gimdbach. |

EXAMPLE 1

Depending on the choice of active substances, the following step 1.1 for preparing an excipient mixture may not be necessary. If the desired powder mixture is to contain only excipient of a uniform coarser particle size distribution in addition to the active substance, the procedure may continue directly according to step 1.2.

1.1: Excipient Mixture:

31.82 kg of lactose monohydrate for inhalation (200M) are used as the coarser excipient component, 1.68 kg of lactose monohydrate (5 μm) are used as the finer excipient component. In the resulting 33.5 kg of excipient mixture the proportion of the finer excipient component is 5%.

About 0.8 to 1.2 kg of lactose monohydrate for inhalation (200M) are added to a suitable mixing container through a suitable granulating sieve with a mesh size of 0.5 mm. Then alternate layers of lactose monohydrate (5 μm) in batches of about 0.05 to 0.07 kg and lactose monohydrate for inhalation (200M) in batches of 0.8 to 1.2 kg are sieved in. Lactose monohydrate for inhalation (200M) and lactose monohydrate (5 μm) are added in 31 and 30 layers, respectively (tolerance: ±6 layers).

The ingredients sieved in are then mixed together with a gravity mixer (mixing at 900 rpm).

1.2: Powder Mixture Containing Active Substance:

To prepare the final mixture, 32.87 kg of the excipient mixture (1.1) and 0.13 kg of micronised tiotropium bromide monohydrate are used. The content of active substance in the resulting 33.0 kg of inhalable powder is 0.4%.

About 1.1 to 1.7 kg of excipient mixture (1.1) are added to a suitable mixing container through a suitable granulating sieve with a mesh size of 0.5 mm. Then alternate layers of tiotropium bromide monohydrate in batches of about 0.003 kg and excipient mixture (1.1) in batches of 0.6 to 0.8 kg are sieved in. The excipient mixture and the active substances are added in 46 or 45 layers, respectively (tolerance: ±9 layers).

The ingredients sieved in are then mixed together in a gravity mixer (mixing at 900 rpm). The final mixture is passed through a granulating sieve twice more and then mixed (mixing at 900 rpm).

EXAMPLE 2

Inhalation capsules (inhalettes) having the following composition were produced using the mixture obtained according to Example 1:

| | |
|---|---|
| tiotropium bromide monohydrate: | 0.0225 mg |
| lactose monohydrate (200 M): | 5.2025 mg |
| lactose monohydrate (5 μm): | 0.2750 mg |
| hard gelatine capsule: | 49.0 mg |
| Total: | 54.5 mg |

EXAMPLE 3

Inhalation capsules having the composition:

| | |
|---|---|
| tiotropium bromide monohydrate: | 0.0225 mg |
| lactose monohydrate (200 M): | 4.9275 mg |
| lactose monohydrate (5 μm): | 0.5500 mg |
| hard gelatine capsule: | 49.0 mg |
| Total: | 54.5 mg |

The inhalable powder needed to prepare the capsules was obtained analogously to Example 1.

EXAMPLE 4

Inhalation capsules having the composition:

| | |
|---|---|
| tiotropium bromide monohydrate: | 0.0225 mg |
| lactose monohydrate (200 M): | 5.2025 mg |
| lactose monohydrate (5 μm): | 0.2750 mg |
| polyethylene capsule: | 100.0 mg |
| Total: | 105.50 mg |

The inhalable powder needed to prepare the capsules was obtained analogously to Example 1.

We claim:

1. A process for preparing an inhalable powder, wherein N+m substantially equal portions of an excipient having a larger *average* particle size [distribution] and N equal portions of an active substance having a smaller *average* particle size [distribution] are added in alternate layers into a suitable mixing vessel and after all the excipient and active substance have been added the 2N+m layers of the two components are mixed together using a suitable mixer, wherein a portion of the excipient having the larger particle size is added first, and wherein N is an integer >5 and m denotes 0 or 1.

[2. A process according to claim 1, wherein N is an integer >5.]

3. A process according to claim 1, characterised in that the individual portions of excipient and active substance are added in layers through a suitable screening apparatus.

4. A process according to claim 1, characterised in that m denotes 1.

5. A process according to claim 1, characterised in that the inhalable powder obtained contains less than 5% of active substance.

6. A process according to claim 5, characterised in that the inhalable powder obtained contains less than 2% of active substance.

7. A process according to claim 1, characterised in that the active substance has a*n average* particle size of from 0.5 to 10 μm.

8. A process according to claim 7, characterised in that the active substance has a*n average* particle size of from 1 to 6 μm.

9. A process according to claim 1, characterised in that the excipient has a*n average* [mean] particle size of from 10 to 100 μm.

10. A process according to claim 9, characterised in that the excipient has a*n average* [mean] particle size of from 15 to 80 μm.

11. A process according to claim 1, wherein the excipient is a single excipient or a mixture of different excipients.

12. A process according to claim 1, characterised in that the excipient consists of a mixture of coarser excipient with an average particle size of 15 to 80 μm and finer excipient with an average particle size of 1 to 9 μm, the proportion of finer excipient constituting 1 to 20% of the total amount of excipient.

13. A process according to claim 1, wherein the active substance is a single active substance or two or more different active substances.

14. A process according to claim 1, characterised in that the active substance consists of one or more compounds selected from among the betamimetics, anticholinergics, corticosteroids and dopamine agonists.

15. An inhalable powder obtained by the process according to claim 1.

*16. The process according to claim 1 wherein the active substance is selected from the group consisting of betamimetics, anticholinergics, corticosteroids, dopamine agonists, and pharmaceutically acceptable salts, solvates or hydrates thereof, and mixtures thereof.*

*17. The process according to claim 16 wherein the active substance consists of an anticholinergic compound or its pharmaceutically acceptable solvate, hydrate or salt.*

*18. The process according to claim 17 wherein the anticholinergic compound comprises tiotropium.*

*19. The process according to claim 17 wherein the pharmaceutically acceptable salt of the anticholinergic compound comprises tiotropium bromide.*

*20. The process according to claim 17 wherein the pharmaceutically acceptable solvate or hydrate of the anticholinergic compound comprises tiotropium bromide monohydrate.*

*21. The process according to claim 1 wherein the excipient is selected from the group consisting of monosaccharides, disaccharides, oligosaccharides, polysaccharides, polyalcohols, salts, and mixtures thereof, each optionally in its hydrate forms.*

*22. The process according to claim 21 wherein the excipient consists of a monosaccharide or a disaccharide, or a combination thereof.*

*23. The process according to claim 21 wherein the excipient consists of glucose or lactose or a combination thereof, each optionally in its hydrate form.*

*24. The process according to claim 22 wherein the excipient consists of a disaccharide.*

*25. The process according to claim 23 wherein the excipient consists of lactose or lactose monohydrate.*

*26. The inhalable powder according to claim 15 wherein the active substance is selected from the group consisting of betamimetics, anticholinergics, corticosteroids, dopamine agonists, and pharmaceutically acceptable salts, solvates or hydrates thereof, and mixtures thereof.*

*27. The inhalable powder according to claim 26 wherein the active substance consists of an anticholinergic compound or its pharmaceutically acceptable solvate, hydrate or salt.*

*28. The inhalable powder according to claim 27 wherein the anticholinergic compound consists of tiotropium.*

*29. The inhalable powder according to claim 27 wherein the pharmaceutically acceptable salt of the anticholinergic compound consists of tiotropium bromide.*

*30. The inhalable powder according to claim 27 wherein the pharmaceutically acceptable solvate or hydrate of the anticholinergic compound consists of tiotropium bromide monohydrate.*

*31. The inhalable powder according to claim 1 wherein the excipient is selected from the group consisting of monosaccharides, disaccharides, oligosaccharides, polysaccharides, polyalcohols, salts, and mixtures thereof, each optionally in its hydrate form.*

*32. The inhalable powder according to claim 31 wherein the excipient consists of a monosaccharide or a disaccharide or a combination thereof.*

*33. The inhalable powder according to claim 32 wherein the excipient consists of glucose or lactose or combinations thereof, each optionally in its hydrate form.*

*34. The inhalable powder according to claim 32 wherein the excipient consists of a disaccharide.*

*35. The inhalable powder according to claim 33 wherein the excipient consists of lactose or lactose monohydrate.*

* * * * *